United States Patent
Park et al.

(10) Patent No.: US 7,283,873 B1
(45) Date of Patent: Oct. 16, 2007

(54) MONITORING AND SYNCHRONIZING VENTRICULAR CONTRACTIONS USING AN IMPLANTABLE STIMULATION DEVICE

(75) Inventors: Euljoon Park, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 330 days.

(21) Appl. No.: 10/838,692

(22) Filed: May 3, 2004

(51) Int. Cl.
*A61N 1/362* (2006.01)

(52) U.S. Cl. .......................................... 607/16; 607/17
(58) Field of Classification Search ................ 600/486; 607/17–19
See application file for complete search history.

(56) References Cited

U.S. PATENT DOCUMENTS

| | | | |
|---|---|---|---|
| 5,300,093 A | 4/1994 | Koestner et al. ............... 607/32 |
| 5,417,717 A | 5/1995 | Salo et al. ..................... 607/18 |
| 5,814,076 A * | 9/1998 | Brownlee ....................... 607/9 |
| 6,070,100 A | 5/2000 | Bakels et al. .................. 607/9 |
| 6,223,082 B1 | 4/2001 | Bakels et al. .................. 607/17 |
| 6,280,389 B1 * | 8/2001 | Ding et al. .................... 600/485 |
| 6,738,667 B2 * | 5/2004 | Deno et al. .................... 607/23 |
| 6,754,530 B2 | 6/2004 | Bakels et al. .................. 607/14 |
| 2002/0143368 A1 | 10/2002 | Bakels et al. .................. 607/9 |
| 2006/0271119 A1 * | 11/2006 | Ni et al. ....................... 607/9 |

* cited by examiner

*Primary Examiner*—Carl Layno
*Assistant Examiner*—Brian T. Gedeon

(57) ABSTRACT

An implantable cardiac stimulation device is configured to measure selected ventricular contraction parameters and apply stimulation therapy based on an analysis of the ventricular contraction parameters. The ventricular contraction parameters may include impedance values that correspond to the volume of fluid in the right ventricle and the left ventricle. The ventricular contraction parameters may include motion values that correspond to heart sounds/motion in the right ventricle and the left ventricle. The ventricular contraction parameters can be used to form a ventricular parameter loop associated with one or more cardiac cycles. The total area within the resulting loop should be maintained below a threshold value through the application of applicable stimulation therapy and/or further physician assistance.

32 Claims, 9 Drawing Sheets

MONITORING AND SYNCHRONIZING VENTRICULAR CONTRACTIONS USING AN IMPLANTABLE STIMULATION DEVICE

RELATED PATENT APPLICATIONS

This application is related to U.S. patent applications Ser. No. 10/838,947, titled "Monitoring Ventricular Contractions Using an Implantable Stimulation Device"; and Ser. No. 10/838,939, titled "Monitoring Ventricular Contractions Using an Implantable Stimulation Device", filed May 3, 2004, and which are incorporated herein in their entirety by reference.

TECHNICAL FIELD

Exemplary methods and apparatuses presented herein generally relate to cardiac pacing devices and more particularly to detecting unsynchronized ventricular contractions and apply responsive stimulation therapy and/or report such information for further consideration.

BACKGROUND

Congestive heart failure (CHF) is a disease condition that involves the loss of pumping ability by the heart. Often CHF is accompanied by fluid accumulation in the body tissues, and especially in the lungs. CHF usually develops slowly, such that symptoms may not appear until the condition has progressed over time. This is because the heart deals with and essentially hides the underlying problems by making adjustments that delay—but do not prevent—the eventual loss in pumping capacity. For example, the heart may cope with and hide the effects of CHF by enlarging (i.e., dilatation) to allow more blood to enter into the heart. The muscle fibers of the heart may also thicken (i.e., hypertrophy) to strengthen the heart muscle and thereby contract more forcefully and pump more blood. The heart may also beat more often to increase circulation. By making these adjustments, or compensating, the heart can temporarily make up for losses in pumping ability, sometimes for years. However, compensation has its limits. Eventually, the heart cannot offset the lost ability to pump blood, and the signs of CHF will appear.

Traditionally, a patient afflicted with CHF would receive drug therapy and make healthy lifestyle changes. Recently, there has been a movement towards further treating certain CHF patients with pacing therapy. Here, it has been found that the contractions of the left ventricle and the right ventricle may become unsynchronized, for example, as a result of a bundle branch block. This loss of synchronization between the left and right ventricles can significantly reduce the heart's pumping ability. Implantable pacing devices can be configured to apply therapy (e.g., bi-ventricular pacing) to selected areas of the heart to improve the heart's pumping ability. However, before shock therapy can be applied, there is a need to determine the applicable pacing parameters for the patient.

U.S. Pat. No. 6,280,389, issued to Ding et al., titled "Patient Identification for the Pacing Therapy Using RV-LV Pressure Loop", teaches that not all CHF patients may benefit from pacing therapy. Here, for example, Ding et al. provide methods for determining if a CHF patient may benefit from pacing therapy based on measured pressure levels within the left ventricle (LV) and right ventricle (RV). The measured pressure level data can be plotted to form a loop. Based on this RV-LV pressure loop, it can be determined whether a CHF patient should receive pacing therapy.

Measuring the pressure within the RV and LV can be accomplished during acute treatment, for example, within a hospital setting wherein catheters having leads with pressure sensors may be placed within each ventricular chamber. However, such sensors may not be suited for chronic diagnostics and treatment using an implantable device. There is significant trepidation in placing leads within the LV during chronic treatment, since the blood pressure within this chamber is much higher compared to the RV. There is a danger, should a lead break within the LV, that the broken piece(s) may flow with the blood to the patient's brain and cause a stroke.

Consequently, there is a need for methods and apparatuses that can detect unsynchronized ventricular contractions and selectively apply responsive pacing therapy and/or report such information for further consideration by a physician. Preferably, the methods and apparatuses can be employed within implantable devices used for chronic treatment of CHF and other heart diseases.

SUMMARY

The above stated needs and others are met, for example, by a method for use with an implantable cardiac stimulation device. The method includes using the implantable cardiac stimulation device to collect (i.e., detect and measure) right ventricle (RV) contraction parameters and left ventricle (LV) contraction parameters during the at least one cardiac cycle. For the patient's safety, the LV contraction parameters are preferably not collected with a pressure sensor within the left ventricle.

The method further includes processing the RV and LV contraction parameters to produce corresponding ventricular contraction loop data. This ventricular contraction loop data includes information about how well the left and right ventricles are synchronized and pumping blood. Such information may then be used to apply/adjust stimulation therapy to at least one of the ventricles and/or possibly be used to alert the patient/doctor about the patient's condition.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1A:
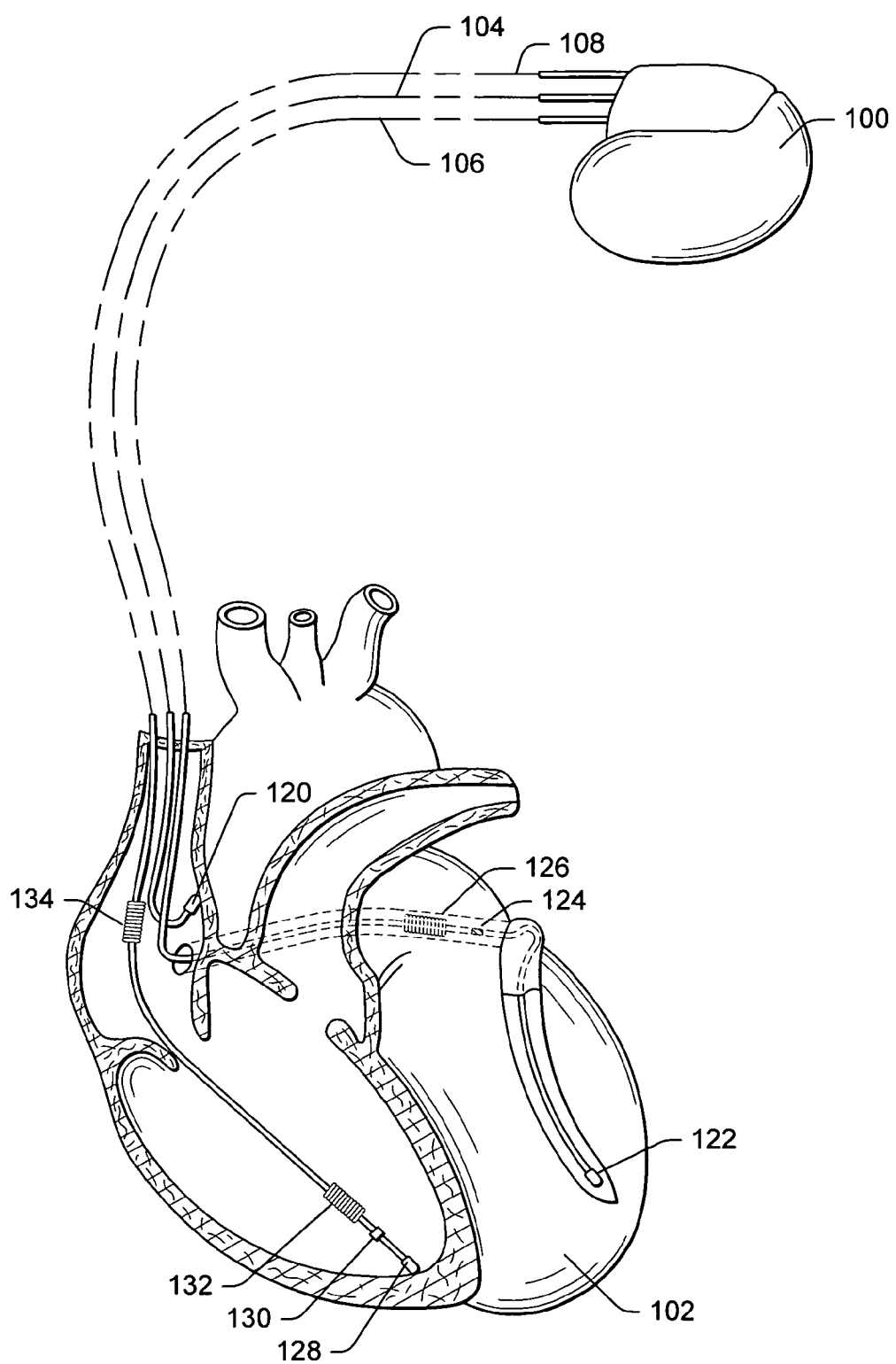
FIG. 1A is simplified diagram illustrating an implantable stimulation device that is configured to detect ventricular contractions based on measured impedance values and selectively apply responsive pacing therapy and/or report such information for further consideration by a physician.

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Two exemplary techniques are described for determining if a patient's RV and LV are properly synchronized, and if not, reporting such information to the patient's physician and/or selectively applying the applicable stimulation to the heart to improve synchronization between the RV and LV contractions. These techniques can be accomplished using conventional leads and do not require the use of pressure sensors and/or placing a lead within the LV.

The first technique allows an implantable stimulation device to detect RV and LV contractions based on measured impedance values. The measured impedance values may be collected using a case lead, an RV lead and either a transseptal LV lead, an LV lead placed through the coronary sinus, or the like. When the applicable conductors within the leads are positioned correctly, the measured impedance values collected will significantly correlate to the volume of blood present within each of the ventricles as they contract.

As is known, the volume of blood within each ventricle can be associated with the internal ventricular pressure to form a pressure-volume (P-V) loop for each cardiac cycle, and similarly an RV-LV volume loop, each of which can be very useful in diagnosing and treating CHF patients.

As shown herein, a pseudo RV-LV volume loop can be advantageously generated using the measured impedance values for each of the ventricles during one or more cardiac cycles. The resulting RV-LV impedance loop is then used to selectively apply responsive pacing therapy and/or report such information for further consideration by a physician. The RV-LV impedance loop can be used to assist in the optimal programming of multi-chamber pacing parameters. The RV-LV impedance loop can also be used to help guide the leads to optimal positions during implantation.

The second technique provides the same benefits, but utilizes leads having motion detection sensors, such as, accelerometers, to detect heart sounds and/or motion associated with the cardiac cycle, and in particular ventricular systole. The motion data that is collected can be converted into corresponding displacement values for each ventricle. These RV and LV displacement values can be processed to form an RV-LV displacement loop that can be used similar to the RV-LV impedance loop.

Exemplary Stimulation Device

The techniques described below are intended to be implemented in connection with any stimulation device that is configured or configurable to stimulate or shock a patient's heart. While the examples described below illustrate implantable stimulation devices with three leads having various components, it should be understood that the techniques herein can be applied to devices having two or more leads, and the leads in certain implementations may be unipolar.

With this in mind, FIG. 1A shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the LV and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least an LV tip electrode 122, left atrial pacing therapy using at least a left atrial ring electrode 124, and shocking therapy using at least a left atrial coil electrode 126.

Stimulation device 100 is also shown in electrical communication with the patient's heart 102 by way of an implantable RV lead 108 having, in this implementation, a RV tip electrode 128, a RV ring electrode/sensor 130, an RV coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, RV lead 108 is capable of receiving cardiac signals, and delivering stimulation in the form of pacing and shock therapy to the right ventricle.

Stimulation device 100 can be configured to measure impedance values for each of the ventricles. Preferably, multiple impedance values are collected over one or more cardiac cycles. Each measured impedance value will be significantly correlated to the volume of blood present in the applicable ventricle at the time of measurement, as blood tends to provide a much better electrical conductor than the surrounding tissues. As a result, lower impedance values will be measured when a ventricle is full of blood (pre-ejection) and higher impedance values will be measured once the ventricle has contracted and ejected most of the blood. Thus, the measured impedance values are significantly correlated to the volume of blood within the ventricle.

To measure the impedance values for the RV, for example, a known current can be passed between a device case or housing electrode (e.g., 100) and an electrode provided within the RV, such as, a RV tip electrode 128, a RV ring electrode/sensor 130 or an RV coil electrode 132. Preferably, the case electrode and RV electrode will be positioned such that the intervening volume of pre-election blood in the RV will provide a significant conductive path for the known current signal. The voltage drop through the resulting conductive path(s) is measured. The measured impedance can then be determined by applying Ohm's law using the known current and measured voltage value.

Similarly, to measure the impedance values for the LV, a known current can be passed between an electrode within the RV and an electrode configured for the LV. Thus, for example, a known current can be passed between RV tip electrode 128 and LV tip electrode 122. Preferably, the RV and LV electrodes will be positioned such that the intervening volume of pre-election blood in the LV will provide a significant conductive path for the known current signal. Thus, as with the RV, the voltage drop through the resulting LV related conductive path is measured and the measured impedance determined by applying Ohm's law using the known current and measured voltage value.

Figure 1B:
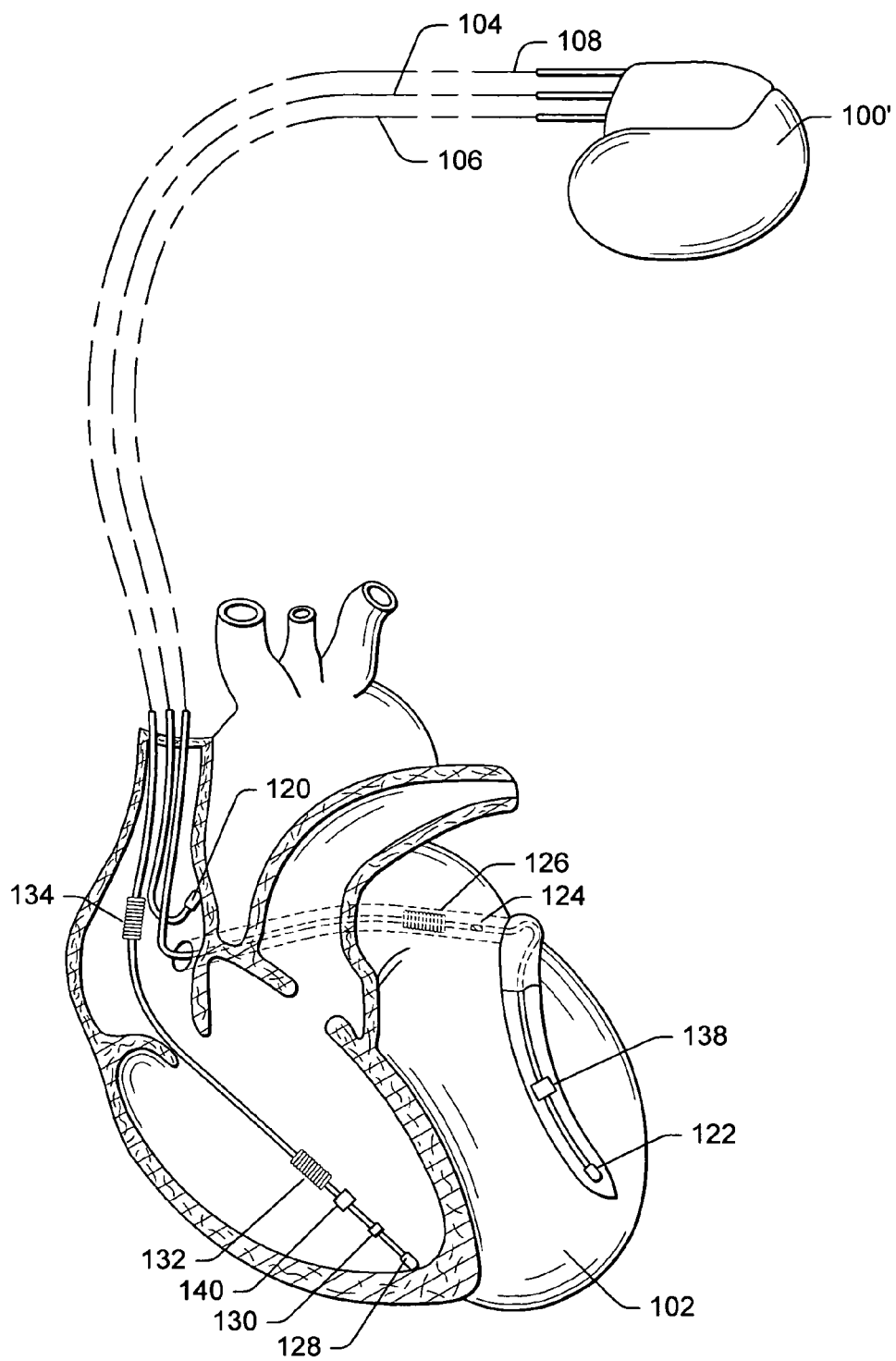
FIG. 1B is simplified diagram illustrating an implantable stimulation device that is configured to detect ventricular contractions based on measured physical motion values and selectively apply responsive pacing therapy and/or report such information for further consideration by a physician.

Reference is now made to FIG. 1B, which is similar to FIG. 1A. Here, however, stimulation device 100' is further provided with an LV motion sensor 138 operatively provided in the coronary sinus lead 106 and an RV motion sensor 140 provided in RV lead 108. Motion sensors 138 and 140 are basically configured to detect motion associated with "heart sounds", such as the sounds of the mitral valve closing and opening, and/or other ventricular movement. Motion sensors 138 and 140 include accelerometers that convert physical cardiac movements into corresponding acceleration signals. The measured acceleration signals (values) can then be integrated or otherwise similarly converted to form velocity values, which can then be integrated or otherwise similarly converted to form displacement values.

Figure 2A:
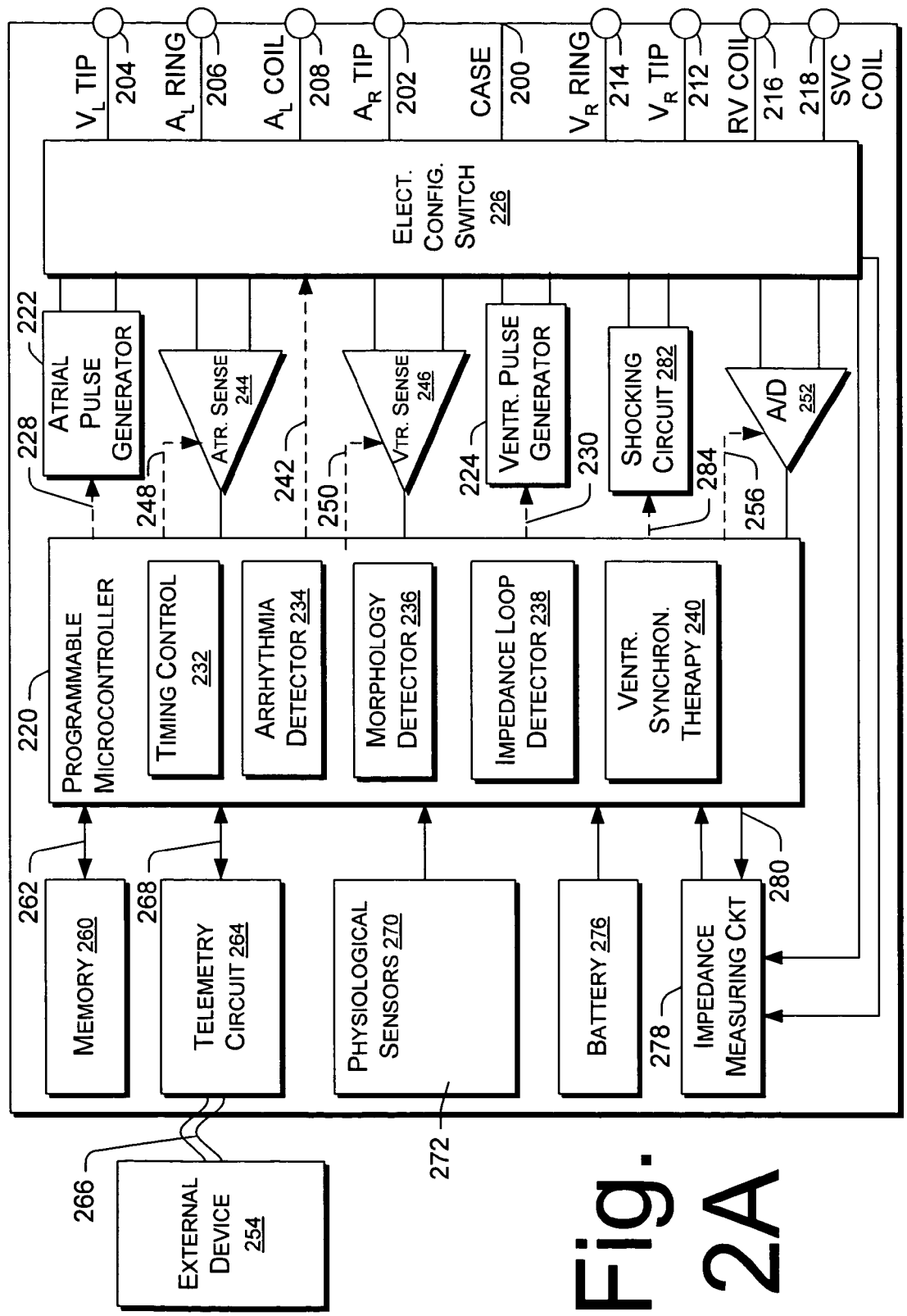
FIG. 2A is a functional block diagram depicting selected features of an implantable stimulation device, for example, as in FIG. 1A.

Attention is now drawn to FIG. 2A, which depicts an exemplary, simplified block diagram depicting various components of stimulation device 100, e.g., as in FIG. 1A.

Stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

At the core of stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

FIG. 2A also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, an impedance loop detector 238, and a ventricular synchronization module 240. These components can be utilized by stimulation device 100 for determining desirable times to administer various therapies, including those that take advantage of the RV-LV impedance loop information, as will become more apparent below. The components 234-240 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224, respectively, in a demand fashion in response to the absence or presence of cardiac activity in the appropriate chambers of the heart. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 may be coupled to the microcontroller 220, or other detection circuitry, for detecting an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262, wherein the programmable operating parameters used by the microcontroller 220 are stored and modified, as required, in order to customize the operation of stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

Stimulation device 100 can further include one or more physiologic sensors 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within stimulation device. 100, it is to be understood that the physiologic sensor 270 may also be external to stimulation device 100, yet still be implanted within or carried by the patient. Examples of physiologic sensors that may be implemented in device 100 include known sensors that, for example, sense respiration rate and/or minute ventilation, pH of blood, ventricular gradient, and so forth. The physiological sensors 270 may further include a pressure sensor that is coupled to detect RV pressure that is sensed by a sensor located at ring 130, which can perform dual functions of a ring electrode and a pressure sensor.

The stimulation device additionally includes a battery 276 that provides operating power to all of the circuits shown in FIG. 2. For stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium/silver vanadium oxide batteries, as is true for most (if not all) current devices.

Stimulation device 100 can further include magnet detection circuitry (not shown), coupled to the microcontroller 220, to detect when a magnet is placed over stimulation device 100. A magnet may be used by a clinician to perform various test functions of stimulation device 100 and/or to signal the microcontroller 220 that the external programmer 254 is in place to receive or transmit data to the microcontroller 220 through the telemetry circuits 264.

Stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where stimulation device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (up to 0.5 Joules), moderate (0.5-10 Joules), or high energy (11 to 40 Joules), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In accordance with certain implementations, an impedance loop detector 238 is provided to coordinate the application of a known current through the selected electrodes, and to collect and process, as necessary, impedance values output by impedance measuring circuit 278. Impedance loop detector 238 can also support for the reporting of collected impedance data and/or other related data to external device 254. Additional functionality is provided by a ventricular synchronization therapy module 240, which is configured to cause stimulation therapy to be applied based, at least in part, on a determined RV-LV impedance loop or other like RV-LV impedance information. Here, for example, the stimulation therapy may be applied to one or both of the ventricles.

Figure 2B:
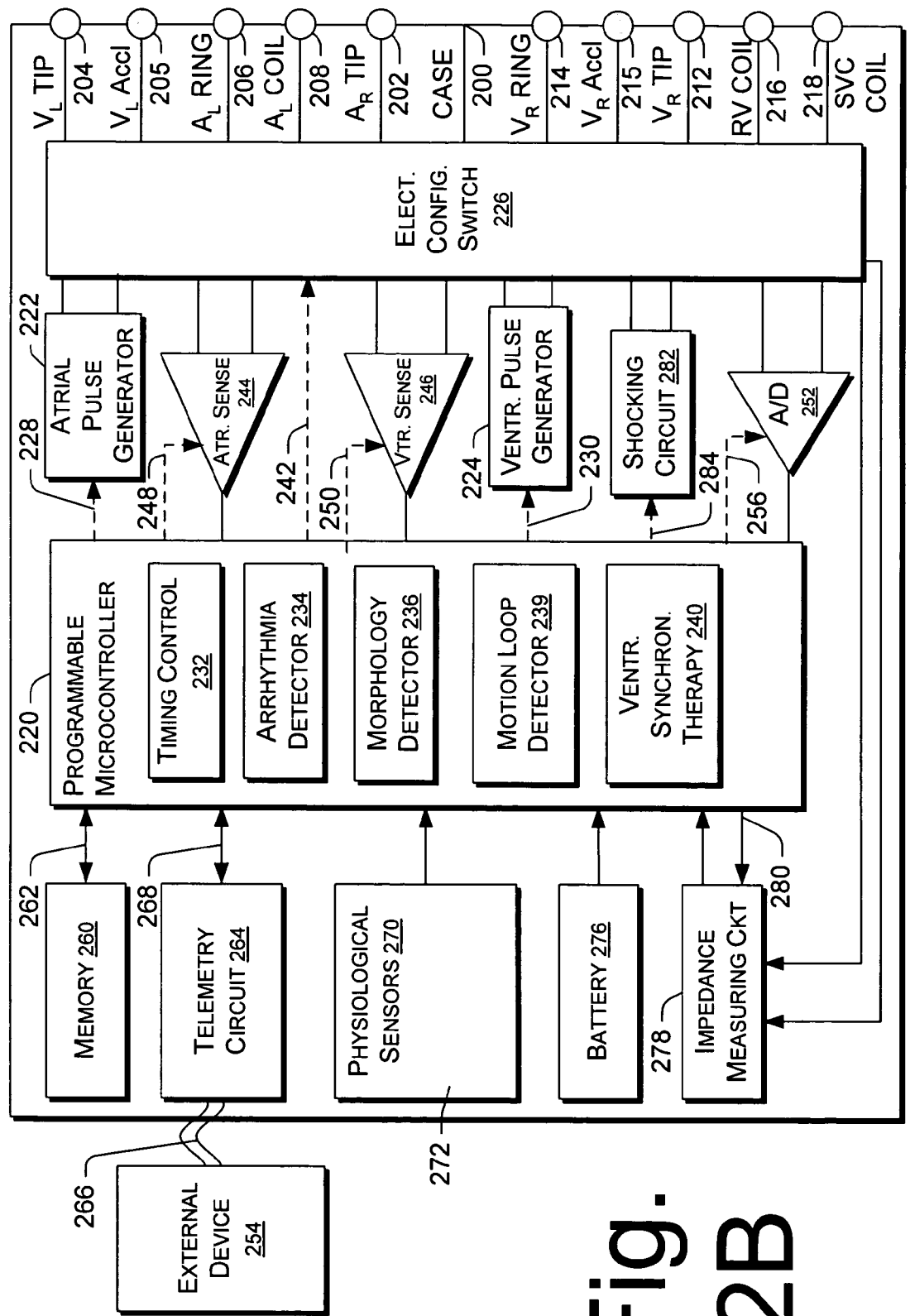
FIG. 2B is a functional block diagram depicting selected features of an implantable stimulation device, for example, as in FIG. 1B.

Reference is now made to FIG. 2B, which is similar to FIG. 2A, except that in this exemplary implementation an LV accelerometer terminal ($V_L$ Accl) 205 and an RV accelerometer terminal ($V_R$ Accl) 215 have been added to switch 226 such that measured acceleration signals/values from LV motion sensor 138 and RV motion sensor 140, respectively, can be received and processed. Also, programmable microcontroller 220 further includes a motion loop detector 239 that is configured to process the measured acceleration values. Motion loop detector 239 can also be configured to support the reporting of collected motion data and/or other related data, to external device 254.

Once again, additional functionality is provided by ventricular synchronization therapy module 240, which is configured to cause stimulation therapy to be applied based, at least in part, on a determined RV-LV displacement loop or other like RV-LV motion information. The resulting stimulation therapy may be applied to one or both of the ventricles.

Exemplary Cardiac Cycle

Figure 3:
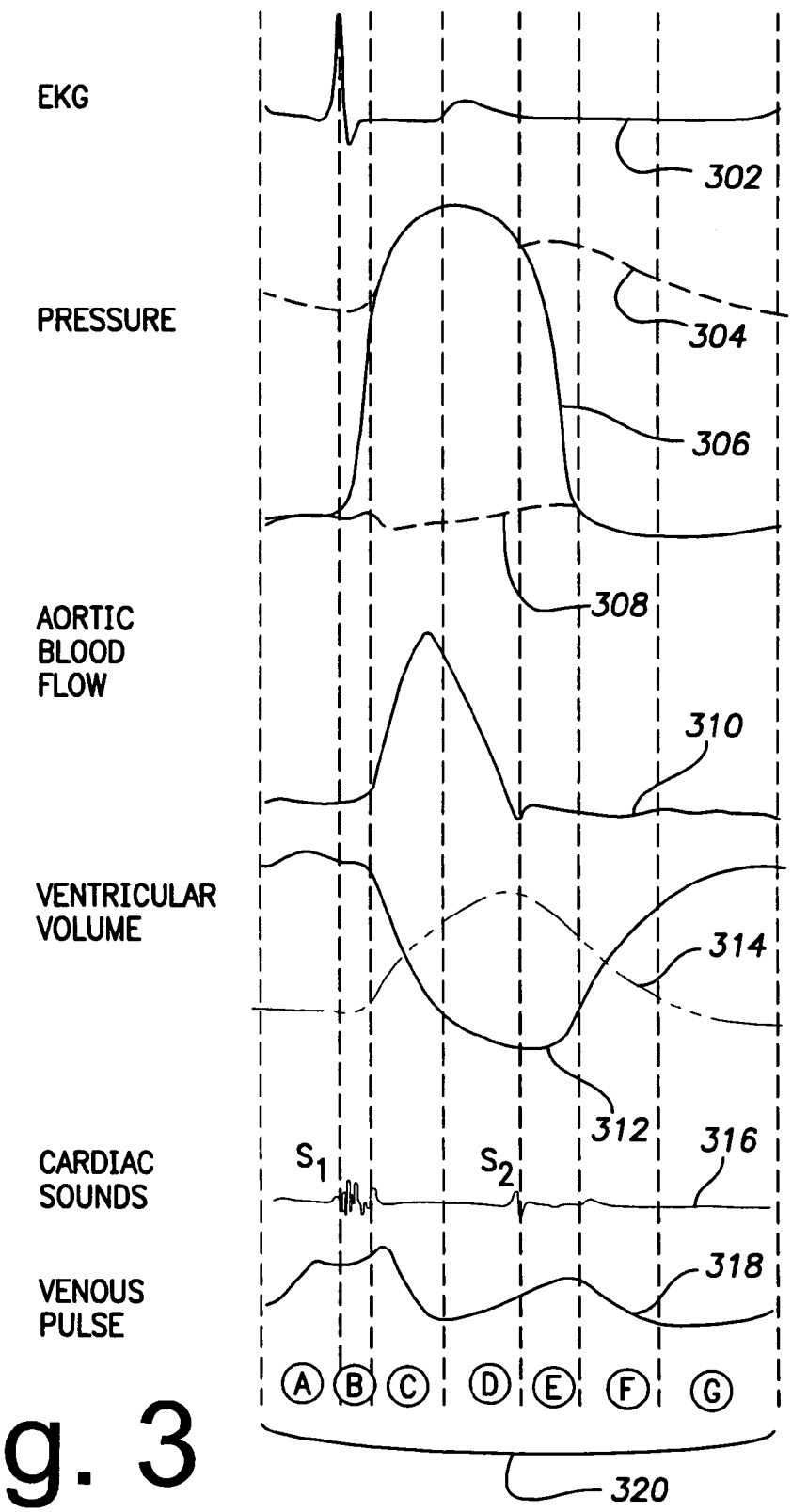
FIG. 3 depicts a collection of plotted values associated with cardiac activity.

FIG. 3 depicts a collection of plotted values associated with cardiac activity, in accordance with certain exemplary implementations. Line 302, at the top of FIG. 3 shows the EKG signal for one cardiac cycle. Below it, line 304 shows the corresponding aortic pressure; line 306 shows the corresponding left ventricular pressure; and, line 308 shows the corresponding left atrial pressure.

Next, line 310 shows the aortic blood flow during the cardiac cycle. Line 312 shows the ventricular volume, which can be compared to line 306 to demonstrate that there is a correspondence between ventricular pressure and ventricular volume. Imposed over line 312, is a dashed line 314 that represents the amplitude of impedance values (e.g., a Z curve) measured using electrical signals passing through the left ventricle. As can be seen, there is an inverse proportional relationship between lines 312 and 314. Hence, there is a relationship between pressure, volume and measurable ventricular impedance.

Line 316 shows the corresponding cardiac sounds (i.e., a phonocardiogram), and in particular detectable $S_1$ and $S_2$ components relating to, in this example, the closing and opening, respectively, of the mitral valve during the cardiac cycle.

Finally, at the bottom of FIG. 3, line 318 shows the corresponding venous pulse.

Circled letters 320 are shown at the bottom of FIG. 3. These letters 320 illustrate certain the periods of the cardiac cycle as defined between dotted lines. Here, letter A marks an atrial systole period; letter B marks a period of isovolumic contraction; letter C marks a period of rapid ejection; letter D marks a period of reduced ejection; letter E marks a period of isovolumic relaxation; letter F marks a period of rapid ventricular filling; and, letter G marks a period of reduced ventricular filling diastasis.

Exemplary RV-LV Impedance Loops

Figure 4:
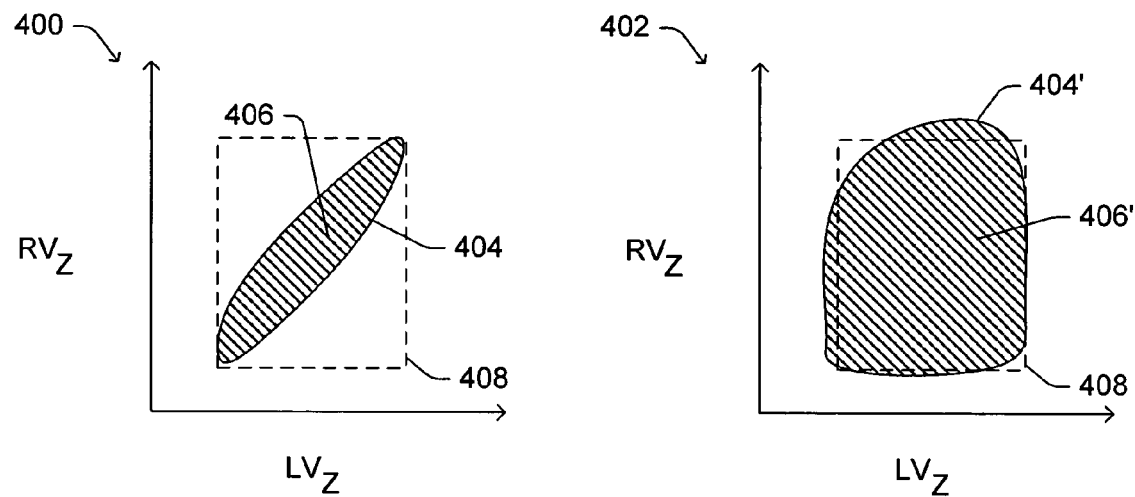
FIG. 4 depicts two graphs, each plotting RV impedance data versus LV impedance data to form RV-LV impedance loops that correlate to RV-LV pressure loops for the same cardiac activity, the first graph is associated with a heart having a healthy synchronized RV-LV contraction and the second graph is associated with a heart having an unhealthy unsynchronized RV-LV contraction.

FIG. 4 depicts two graphs, 400 and 402, each plotting RV impedance data versus LV impedance data to form RV-LV impedance loops that correlate to RV-LV pressure loops for the same cardiac activity. Graph 400 is associated with a heart having a desirable synchronized RV-LV contraction. Graph 402 is associated with a heart having an undesirable, less synchronized RV-LV contraction.

As shown in graph 400, an RV-LV impedance loop 404 can be plotted to encompass an area 406. As represented by the dashed line box 408, a threshold area may be defined such that if area 406 is less than or equal to the threshold area then the heart is functioning within desired bounds.

As illustrated in graph 402, this unhealthy heart leads to loop 404' and an area 406' that is greater than the threshold area represented by box 408. Here, for example, a physician may be alerted to the patient's condition and/or stimulation therapy may be applied/adjusted in an effort to improve the synchronization of the left and right ventricles and bring the area 406' of the loop 404' below the threshold represented by box 408.

Figure 5:
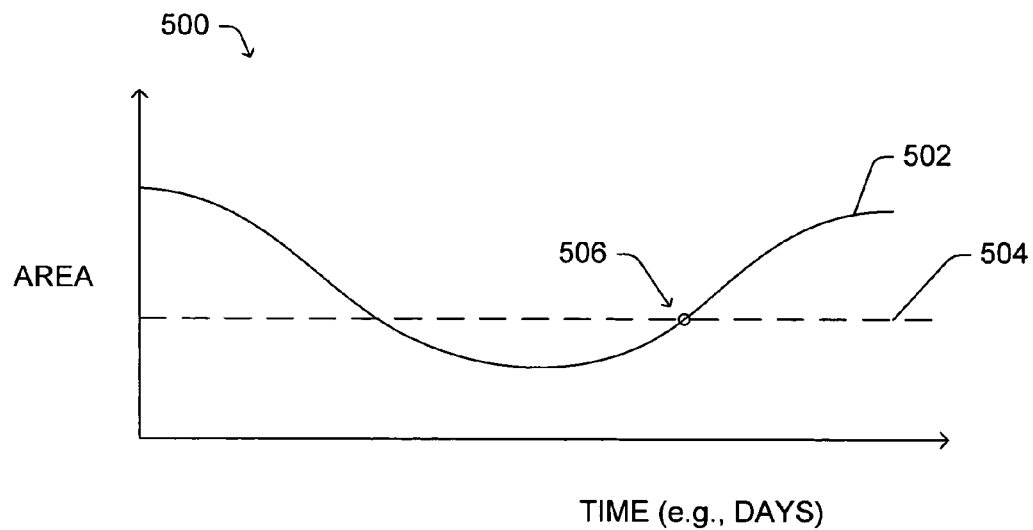
FIG. 5 is a graph depicting a plot of the area of the resulting RV-LV impedance loop, for example, as illustrated in FIG. 4, for a patient that is being monitored over a period of time.

In graph 500, of FIG. 5, line 502 is a running plot of the measured area 406 of the resulting RV-LV impedance loop 404 for a patient that is being monitored over a period of time. A threshold area is represented by line 504. As shown by the downward slope of line 502, the pumping and synchronization of the ventricles was steadily improving and eventually fell within the acceptable region marked by threshold 504. However, as time went on the ventricles started becoming less and less synchronized as illustrated by the increasing slope of line 502. At point 506, the threshold was again exceeded. As such appropriate action, e.g., physician alerting and/or stimulation therapy applied/adjusted, would preferably occur.

Exemplary RV-LV Motion Loops

Figure 6:
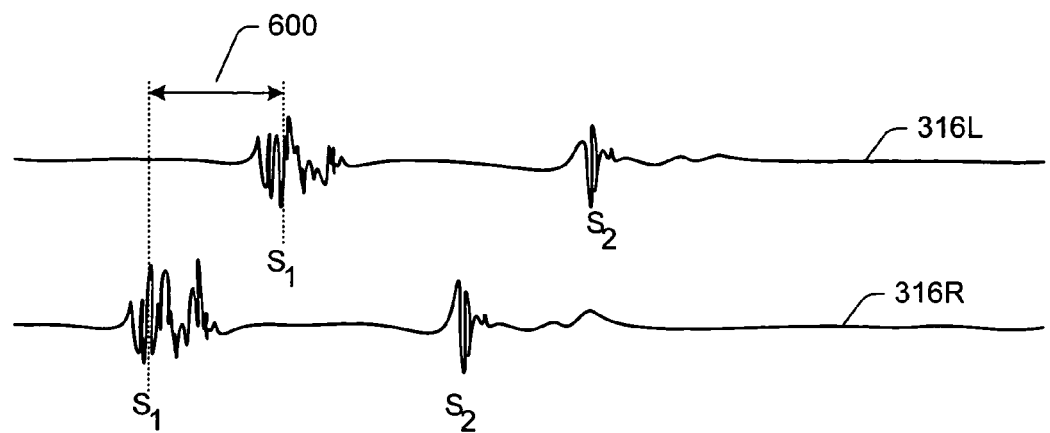
FIG. 6 is an illustrative diagram depicting differences in the sound/motion signals as measured in the RV and LV over a period of time for an unhealthy unsynchronized RV-LV contraction.

FIG. 6 is an illustrative diagram depicting differences in the sound/motion signals 316R and 316L as detected in the RV and LV, respectively during a cardiac cycle. Here, signals 316R and 316L would preferably be more synchronized than shown. Here, an offset 600 illustrates that the heart may be unhealthy in that the ventricles are not sufficiently synchronized during the RV-LV contraction as indicated by the offset of the respective valve closing/opening times.

Figure 7:
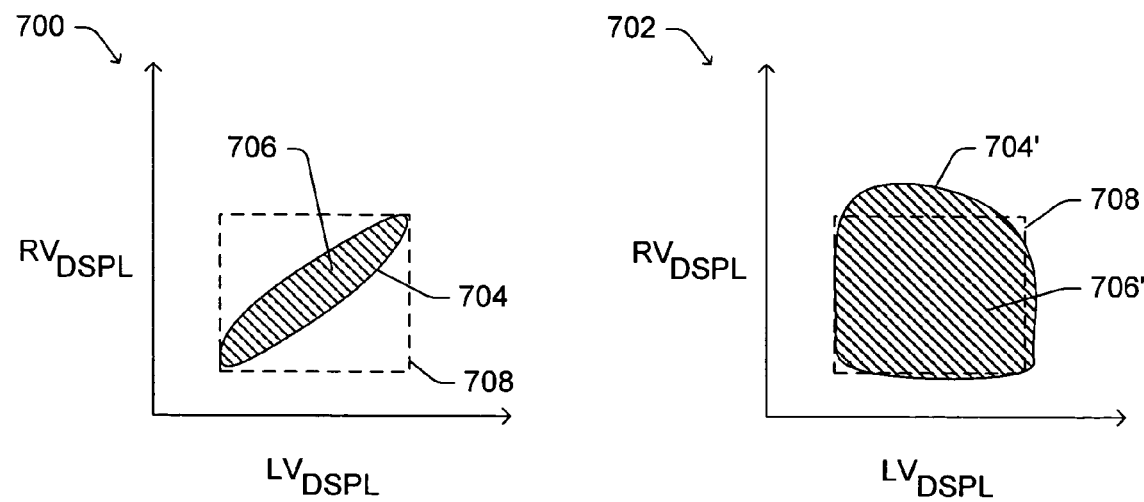
FIG. 7 depicts two graphs, each plotting RV displacement data versus LV displacement data to form RV-LV displacement loops that correlate to RV-LV pressure loops for the same cardiac activity, the first graph is associated with a heart having a healthy synchronized RV-LV contraction and the second graph is associated with a heart having an unhealthy unsynchronized RV-LV contraction.

FIG. 7 depicts two graphs, 700 and 702, each plotting RV displacement data versus LV displacement data to form RV-LV displacement loops that correlate to RV-LV pressure loops for the same cardiac activity. Graph 700 is associated with a heart having a desirable synchronized RV-LV contraction. Graph 702 is associated with a heart having an undesirable, less synchronized RV-LV contraction.

As shown in graph 700, an RV-LV displacement loop 704 can be plotted to encompass an area 706. As represented by the dashed line box 708, a threshold area may be defined such that if area 706 is less than or equal to the threshold area then the heart is functioning within desired bounds.

As illustrated in graph 702, this unhealthy heart leads to loop 704' and an area 706' that is greater than the threshold area represented by box 708. Here, for example, once again a physician may be alerted to the patient's condition and/or stimulation therapy may be applied in an effort to improve the synchronization of the left and right ventricles and bring the area 706' of the loop 704' below the threshold represented by box 408.

Exemplary RV-LV Impedance Loop Process

Figure 8:
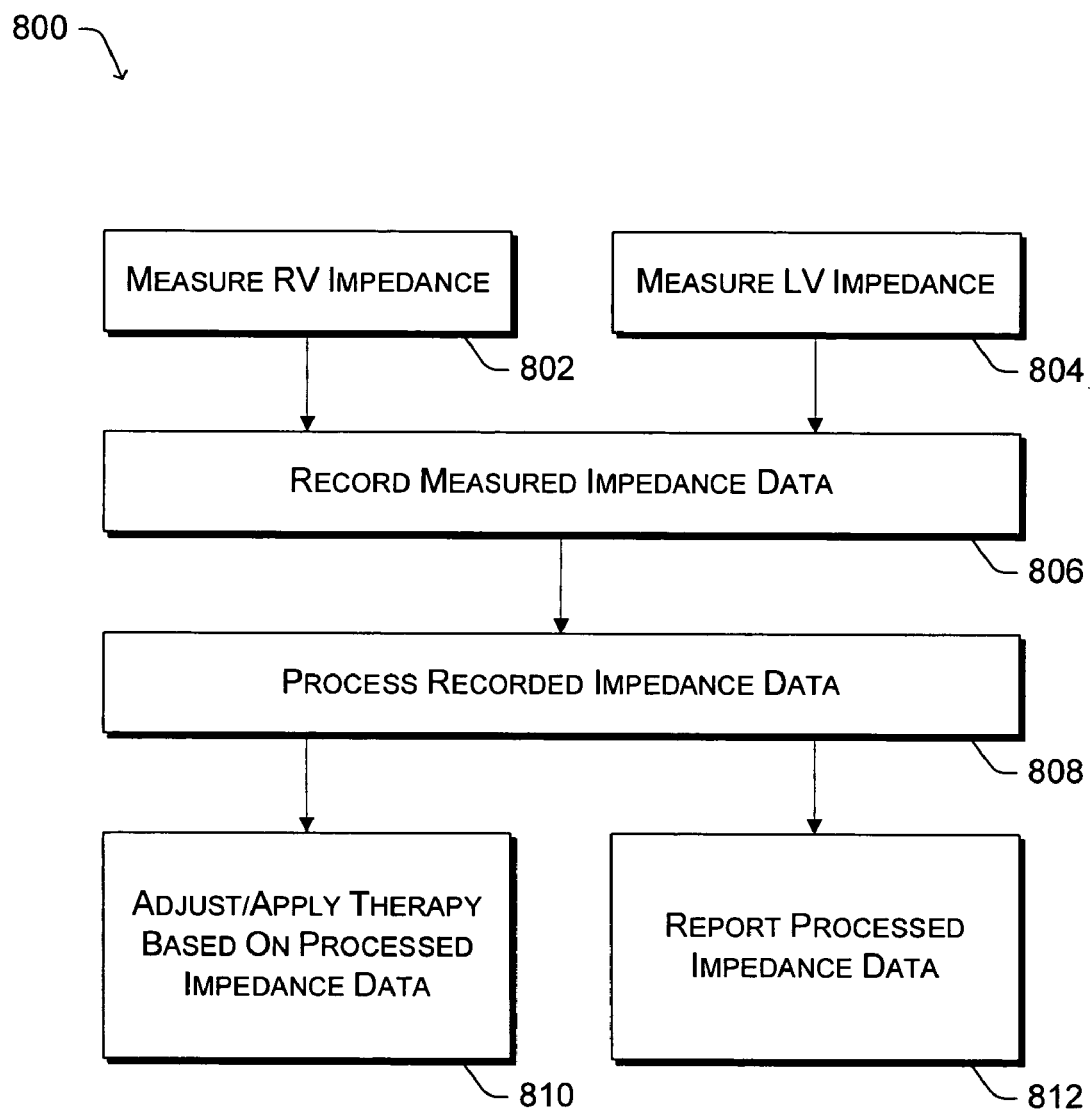
FIG. 8 is a flow diagram illustrating a process for detecting ventricular contractions based on measured impedance values and selectively applying responsive pacing therapy and/or reporting such information for further consideration.

FIG. 8 is a flow diagram illustrating a process 800 for detecting ventricular contractions based on measured impedance values and selectively applying responsive pacing therapy and/or reporting such information for further consideration, in accordance with certain exemplary implementations In step 802, RV impedance values are measured, for example, as described above, and provided to step 806. Similarly and preferably substantially simultaneously, in step 804 corresponding LV impedance values are measured, for example, as described above, and also provided to step 806.

In step 806, the measured RV and LV impedance values (data) are recorded. In step 808, the recorded RV and LV impedance values are processed, for example, to produce RV-LV impedance loop data and related area data. This processed data can then be used to apply/adjust stimulation therapy in step 810, and/or reported out to external device(s) in step 812 for further processing/analysis.

An additional benefit that step 812 may provide is that a physician may consider the processed impedance data during the implantation of the associated lead within the patient. Thus, optimal lead position may be found by examining the processed impedance data.

Exemplary RV-LV Motion Loop Process

Figure 9:
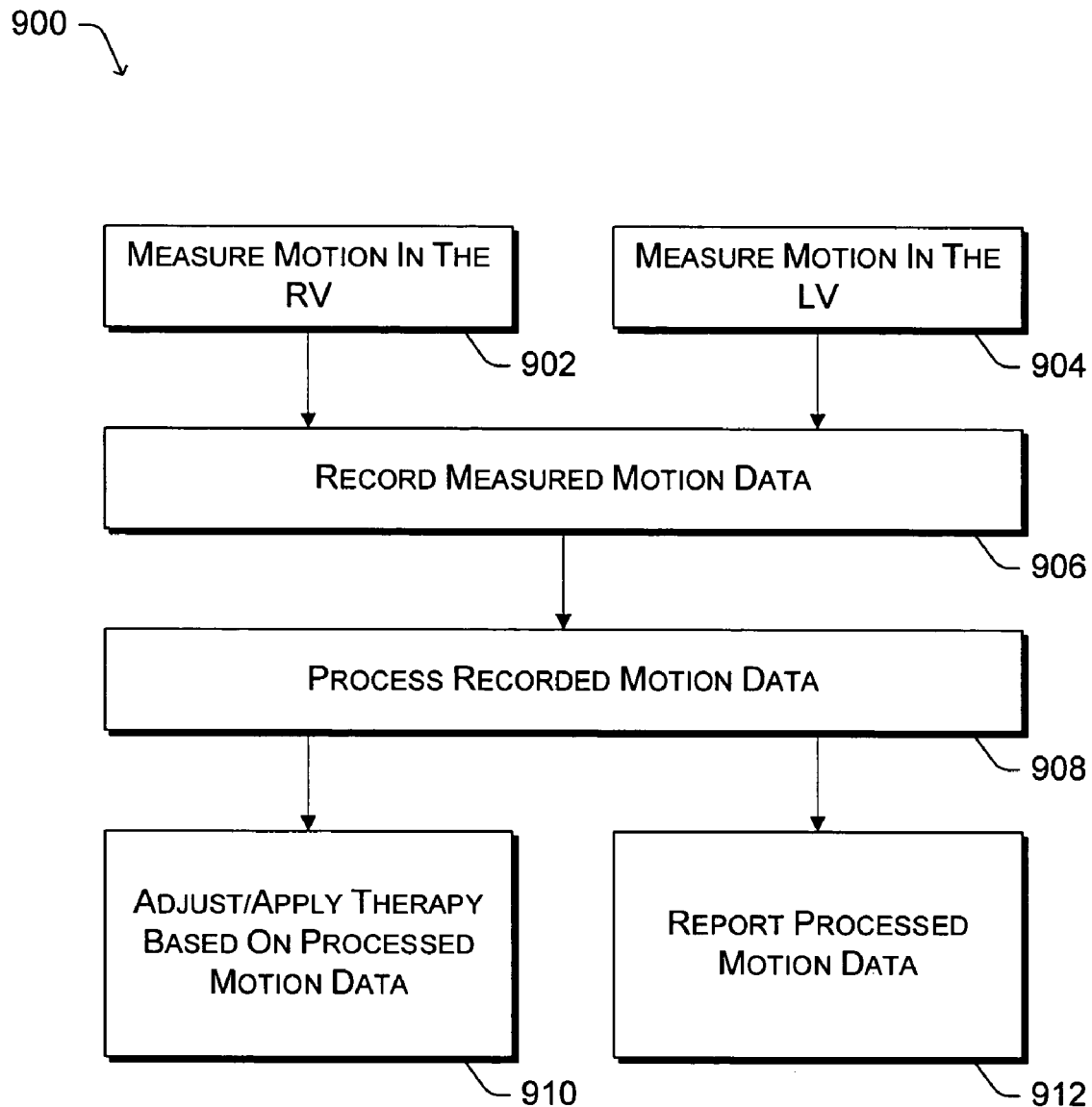
FIG. 9 is a flow diagram illustrating a process for detecting ventricular contractions based on measured physical motion values and selectively applying responsive pacing therapy and/or reporting such information for further consideration.

FIG. 9 is a flow diagram illustrating a process 900 for detecting ventricular contractions based on measured motion values (e.g., sound, acceleration, velocity, displacement, and/or other the like values) and selectively applying responsive pacing therapy and/or reporting such information for further consideration, in accordance with certain exemplary implementations In step 902, RV motion values are measured, for example, as described above, and provided to step 906. Similarly and preferably substantially simultaneously, in step 904 corresponding LV motion values are measured, for example, as described above, and also provided to step 906.

In step 906, the measured RV and LV motion values (data) are recorded. In step 908, the recorded RV and LV motion values are processed, for example, to produce RV-LV motion loop data and related area data. This processed data can then be used to apply/adjust stimulation therapy in step 910, and/or reported out to external device(s) in step 912 for further processing/analysis.

Once again an additional benefit that step 912 may provide is that a physician may consider the processed motion data during the implantation of the associated lead within the patient. Thus, optimal lead position may be found by examining the processed motion data.

CONCLUSION

Although exemplary methods and apparatuses have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and apparatuses.

What is claimed is:

1. In an implantable cardiac stimulation device, a method comprising:
   collecting a plurality of right ventricle (RV) contraction parameters during at least one cardiac cycle;
   collecting a plurality of left ventricle (LV) contraction parameters during said at least one cardiac cycle, without using a LV pressure sensor, wherein said plurality of LV contraction parameters includes a plurality of LV impedance values and collecting said plurality of LV contraction parameters includes measuring said plurality of LV impedance values using a first electrode having at least one electrical contact within the right ventricle, and a second electrode associated with said left ventricle, said second electrode having at least one electrical contact with cardiac tissue of said left ventricle, said first and second electrodes operatively arranged to pass an electrical signal on a path that includes blood within a chamber of the left ventricle; and
   processing said RV contraction parameters as a function of said LV contraction parameters to produce data corresponding to an RV-LV contraction loop.

2. The method as recited in claim 1, further comprising: with the implantable cardiac stimulation device, applying stimulation therapy to at least one ventricle based on said data corresponding to an RV-LV contraction loop.

3. The method as recited in claim 1, further comprising: causing the implantable cardiac stimulation device to output said data corresponding to an RV-LV contraction loop to at least one external device.

4. The method as recited in claim 1, wherein processing said RV and LV contraction parameters to produce said data corresponding to an RV-LV contraction loop further includes:
   determining an area value as defined by said data corresponding to an RV-LV contraction loop for said at least one cardiac cycle.

5. The method as recited in claim 4, further comprising: with the implantable cardiac stimulation device, applying stimulation therapy to at least one ventricle based on said ventricular contraction loop data to improve efficiency of pumping contractions of the RV and LV.

6. The method as recited in claim 5, further comprising: adjusting said stimulation therapy such that subsequent area values fall within a predetermined range of acceptable area values.

7. The method as recited in claim 4, further comprising: causing the implantable cardiac stimulation device to output said area value to at least one external device.

8. The method as recited in claim 7, further comprising:
   monitoring area values during a period that includes a plurality of cardiac cycles; and
   alerting said external device if said monitoring determines that said area data is not within a predefined range of acceptable area values.

9. The method as recited in claim 1, wherein said plurality of RV contraction parameters includes a plurality of RV impedance values and collecting said plurality of RV contraction parameters includes:
   measuring said plurality of RV impedance values using at least two electrodes that are operatively arranged to pass an electrical signal on a path that includes blood within a chamber of the right ventricle.

10. The method as recited in claim 9, wherein said at least two electrodes includes a first electrode having at least one electrical contact within the right ventricle, and a second electrode associated with a case of the implantable cardiac stimulation device.

11. The method as recited in claim 9, wherein measuring each of said plurality of RV impedance values further includes:
   passing said electrical signal, having a known current value between said at least two electrodes;
   measuring a voltage value for said electrical signal that has passed through intervening tissue and liquids; and
   dividing said measured voltage value by said known current value to produce a measured RV impedance value.

12. The method as recited in claim 1, wherein measuring each of said plurality of LV impedance values further includes:
   passing said electrical signal, having a known current value between said at least two electrodes;
   measuring a voltage value for said electrical signal that has passed through intervening tissue and liquids; and
   dividing said measured voltage value by said known current value to produce a measured LV impedance value.

13. The method as recited in claim 1, wherein said plurality of RV contraction parameters includes a plurality of RV motion values and collecting said plurality of RV contraction parameters includes:
   measuring said plurality of RV motion values using at least one lead that is operatively arranged within a chamber of said RV and responsive to physical motion effecting said chamber.

14. The method as recited in claim 13, wherein said at least one lead includes at least one accelerometer.

15. An implantable cardiac stimulation device comprising:
   means for collecting a plurality of right ventricle (RV) contraction parameters during at least one cardiac cycle;
   means for collecting a plurality of left ventricle (LV) contraction parameters during said at least one cardiac cycle, without using a LV pressure sensor, wherein said plurality of LV contraction parameters includes a plurality of LV impedance values and said means for collecting a plurality of LV contraction parameters includes a first electrode having at least one electrical contact within the right ventricle, and a second electrode associated with said left ventricle, said second electrode having at least one electrical contact with cardiac tissue of said left ventricle, said first and second electrodes operatively arranged to pass an electrical signal on a path that includes blood within a chamber of the left ventricle; and means for processing said RV contraction parameters as a function of said LV contraction parameters to produce data corresponding to an RV-LV contraction loop.

16. The implantable cardiac stimulation device as recited in claim 15, further comprising:

means for applying stimulation therapy to at least one ventricle based on said data corresponding to an RV-LV contraction loop.

17. The implantable cardiac stimulation device as recited in claim 15, further comprising:

means for causing the implantable cardiac stimulation device to output said data corresponding to an RV-LV contraction loop to at least one external device.

18. The implantable cardiac stimulation device as recited in claim 17, further comprising:

means for determining an area value as defined by said data corresponding to an RV-LV contraction loop for said at least one cardiac cycle.

19. The implantable cardiac stimulation device as recited in claim 18, further comprising:

means for applying stimulation therapy to at least one ventricle based on said data corresponding to an RV-LV contraction loop to improve efficiency of pumping contractions of the RV and LV.

20. The implantable cardiac stimulation device as recited in claim 18, further comprising:

means for adjusting said stimulation therapy such that subsequent area values fall within a predetermined range of acceptable area values.

21. The implantable cardiac stimulation device as recited in claim 18, further comprising:

means for outputting said area value to at least one external device.

22. The implantable cardiac stimulation device as recited in claim 21, further comprising:

means for monitoring area values during a period that includes a plurality of cardiac cycles; and means for alerting said external device if said monitoring determines that said area data is not within a predefined range of acceptable area values.

23. The implantable cardiac stimulation device as recited in claim 15, wherein said plurality of RV contraction parameters includes a plurality of RV impedance values and further comprising:

means for measuring said plurality of RV impedance values using at least two leads that are operatively arranged to pass an electrical signal on a path that includes blood within a chamber of the right ventricle.

24. An implantable cardiac stimulation device comprising:

memory;

input/output (I/O) circuitry configurable to make electrical contact with tissue within a patient and exchange information with at least one external device, said I/O circuitry including a first electrode having at least one electrical contact within the right ventricle, and a second electrode associated with said left ventricle, said second electrode having at least one electrical contact with cardiac tissue of said left ventricle, said first and second electrodes operatively arranged to pass an electrical signal on a path that includes blood within a chamber of the left ventricle; and logic operatively coupled to said memory and said I/O circuitry, said logic being configured to collect right ventricle (RV) contraction parameters and left ventricle (LV) contraction parameters from said I/O circuitry, process said RV contraction parameters as a function of said LV contraction parameters to produce data corresponding to an RV-LV contraction loop, and store at least a portion of said data corresponding to an RV-LV contraction loop in said memory, and wherein said RV and LV contraction parameters are collected during at least one cardiac cycle, said portion of said I/O circuitry does not include a lead within a chamber of the left ventricle, and said LV contraction parameters include a plurality of LV impedance values.

25. The implantable cardiac stimulation device as recited in claim 24, wherein said logic is further configured to cause said I/O circuitry to apply stimulation therapy to at least one ventricle based on said data corresponding to an RV-LV contraction loop.

26. The implantable cardiac stimulation device as recited in claim 24, wherein said logic is further configured to cause said I/O circuitry to output said data corresponding to an RV-LV contraction loop to said at least one external device.

27. The implantable cardiac stimulation device as recited in claim 24, wherein said logic is further configured to determine an area value as defined by said data corresponding to an RV-LV contraction loop for said at least one cardiac cycle.

28. The implantable cardiac stimulation device as recited in claim 27, wherein said logic is further configured to cause said I/O circuitry to apply stimulation therapy to at least one ventricle based on at least one said area value to improve efficiency of pumping contractions of the RV and LV.

29. The implantable cardiac stimulation device as recited in claim 28, wherein said logic is further configured to adjusting said stimulation therapy such that subsequent area values fall within a predetermined range of acceptable area values.

30. The implantable cardiac stimulation device as recited in claim 27, wherein said logic is further configured to cause said I/O circuitry to output said area value to said at least one external device.

31. The implantable cardiac stimulation device as recited in claim 27, wherein said logic is further configured to monitor area values during a period that includes a plurality of cardiac cycles, and alert said external device if said area data is not within a predefined range of acceptable area values.

32. The implantable cardiac stimulation device as recited in claim 24, wherein said RV contraction parameters includes a plurality of RV impedance values and said I/O circuitry includes:

at least two leads that can be operatively arranged to pass an electrical signal on a path that includes blood within a chamber of the right ventricle and said I/O circuitry is configurable to measure said plurality of RV impedance values using said at least two leads and provide said RV impedance values to said logic.

* * * * *